Figure 1:
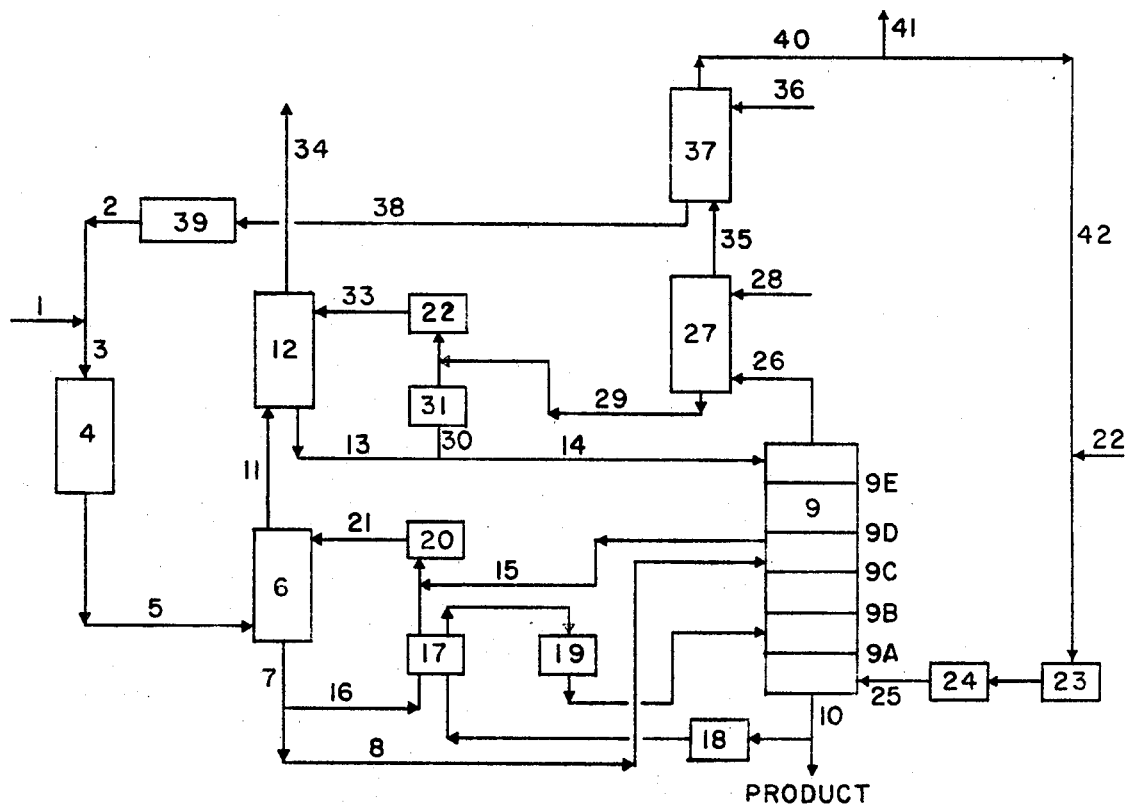

United States Patent [19]

Ferris et al.

[11] 4,348,540
[45] Sep. 7, 1982

[54] MANUFACTURE OF AQUEOUS FORMALDEHYDE

[75] Inventors: Theodore V. Ferris; Richard C. Kmetz, both of Longmeadow, Mass.

[73] Assignee: Monsanto Company, St. Louis, Mo.

[21] Appl. No.: 278,811

[22] Filed: Jun. 29, 1981

[51] Int. Cl.³ .................. B01D 3/16; C07C 47/055; C07C 47/058
[52] U.S. Cl. ............................ 568/472; 568/473; 568/493; 203/42; 203/49; 203/87; 203/98; 203/DIG. 19
[58] Field of Search .............. 568/472, 473, 493; 203/17, 49, 42, 87, DIG. 19, 99, 98, 96; 202/234, 183, 158

[56] References Cited

U.S. PATENT DOCUMENTS

| 2,372,540 | 3/1945 | Balcar | 203/49 |
| 2,565,569 | 8/1951 | McCants | 568/493 |
| 2,675,346 | 4/1954 | MacLean | 568/493 |
| 2,690,994 | 10/1954 | McCants | 203/64 |
| 3,113,972 | 12/1963 | Kodama et al. | 568/473 |
| 3,174,911 | 3/1965 | Webb et al. | 568/493 |
| 3,493,472 | 2/1970 | Schumacher | 568/493 |
| 3,994,977 | 11/1976 | Aicher et al. | 568/473 |
| 4,119,673 | 10/1978 | Aicher et al. | 568/473 |

Primary Examiner—Wilbur L. Bascomb, Jr.
Attorney, Agent, or Firm—R. Bruce Blance; William J. Farrington; Paul D. Matukaitis

[57] ABSTRACT

Formaldehyde manufacture by oxidative-dehydrogenation of methanol over a silver or copper catalyst. Aqueous formaldehyde solution is obtained from the reaction and is stripped of methanol and water by a low energy process at relatively low temperature by means of recycled inert gas in a stripping column comprising at least about 1.5 theoretical transfer units for stripping methanol.

19 Claims, 2 Drawing Figures

MANUFACTURE OF AQUEOUS FORMALDEHYDE

BACKGROUND OF THE INVENTION

This invention relates to a process for the manufacture of formaldehyde by the oxidative dehydrogenation of methanol in the presence of a silver catalyst. More particularly this invention relates to a process for the manufacture of formaldehyde by the oxidative dehydrogenation of methanol in the presence of a silver or copper catalyst in which the aqueous formaldehyde product is stripped of methanol and water by means of an inert gas stream.

In the industrial manufacture of formaldehyde from methanol by dehydrogenating oxidation with air over silver or copper catalyst in the presence of steam, the formaldehyde is usually washed out of or scrubbed from the reaction gas with water. The starting mixture in general contains methanol (calculated as 100% strength) and water in a ratio of from 0.1 to 1.8 moles of water per mole of methanol. On absorption of the reaction mixture, the steam produced by the reaction and the steam and methanol left from the starting mixture are condensed. The formaldehyde combines with water to give methylene glycol and higher polyoxymethylene glycols and with residual methanol to give methyl hemiformal and polyoxymethylene glycol monomethyl ethers. The higher polyoxymethylene glycols tend to precipitate from concentrated aqueous formaldehyde solutions as paraform. Hence aqueous formaldehyde has been conveniently used at a concentration of about 30 to about 37% by weight since such solutions are stable over extended periods of time without precipitation of paraformaldehyde and have been conveniently used in the manufacture of phenolic and amino resins.

In more recent times, with the development of improved stabilizers to suppress paraformaldehyde formation, higher concentrations of aqueous formaldehyde have been accepted for the handling of formaldehyde and the manufacture of resins and have provided energy savings since they improve shipping and handling efficiency and reduce the amount of water to be removed from the resin products. Such concentrated solutions are generally prepared by distilling the aqueous formaldehyde solutions formed in absorbers under conditions which allow most of the unconverted methanol to be removed. The distillation step requires high reflux ratios and considerable energy input.

The present invention is an improved process for the preparation of aqueous formaldehyde solutions in which methanol and water are removed from aqueous formaldehyde solution formed in the absorber, by stripping the solution with an inert gas. The solution can be maintained at an elevated temperature during the stripping operation with heat generated in the oxidative-dehydrogenation of the methanol starting material. In contrast with the high reflux ratios required in the removal of methanol and water by distillation, little or no reflux is required and considerable improvement in energy efficiency of the process is realized. By means of the stripping step, a concentrated aqueous formaldehyde solution of low methanol content can be readily obtained and can be used advantageously in the manufacture of phenolic and amino resins and particularly of $C_2$ and higher alkylated amino resins. Methanol contents of less than 2 weight percent are readily obtained.

In summary the invention is a process for the manufacture of an aqueous solution of formaldehyde comprising the steps of:

(a) oxidatively dehydrogenating methanol with air in the presence of a silver or copper catalyst and steam at elevated temperature;

(b) absorbing the reaction product in an absorption train comprising one or more absorption stages in series to form an aqueous formaldehyde solution containing free and combined methanol; and (c) stripping the methanol from the aqueous formaldehyde solution with an inert gas stream by countercurrent flow in a stripping column comprising at least about 1.5 theoretical transfer units for methanol stripping, the stripping temperature and the ratio of stripping gas to aqueous formaldehyde being selected to provide a concentration of vapors of aqueous formaldehyde in the gas emerging from the stripping column of no more than about 50 mol percent.

Essentially the process is advantageously carried out continuously in the following sequence:

1. a mixture of water and methanol vapors is mixed with air, the mixture is passed over a silver or copper catalyst bed and the methanol is oxidatively dehydrogenated;

2. the reaction product comprising a gaseous mixture of formaldehyde, steam, residual methanol, nitrogen, carbon dioxide and hydrogen is cooled and fed to an absorber comprising a series of stages containing aqueous formaldehyde solution, each stage being equipped with a circulation loop and a cooling system. Sufficient water or dilute aqueous formaldehyde solution is added to the final absorber stage to maintain the desired concentration of formaldehyde in the final product, and aqueous formaldehyde solution is passed through the absorber countercurrently to the reaction gas mixture to absorb most of the formaldehyde, water and methanol from the gas mixture;

3. aqueous formaldehyde solution is fed from the absorber to a multi-stage stripping column while, countercurrently to the aqueous formaldehyde flowing in the multistage stripping column, a stream of inert gas is circulated to strip some of the residual methanol from the solution and simultaneously some water and formaldehyde;

4. the gas stream which emerges from the stripping column is treated to recover most of the stripped methanol, water and formaldehyde and is recycled to the bottom of the stripper column;

5. the aqueous formaldehyde solution which is drawn from the bottom of the stripping column constitutes the final formalin product from the process.

The inert stripping gas is any non-condensible gas which is inert to or non-reactive with the various components of the aqueous formaldehyde solution. Preferably it is a non-flammable, relatively non-toxic and relatively water-insoluble gas. Thus it is advantageously selected from the group consisting of nitrogen, helium, neon, argon and mixtures thereof.

The operation of the stripping column is dependent on several parameters including temperature of the column, ratio of stripping gas to aqueous formaldehyde solution, the number of ideal stages or theoretical transfer units in the column, the residence time of the aqueous formaldehyde solution and the number of aqueous formaldehyde streams supplied to the stripping column from the absorber.

The temperature of the stripping column can be any temperature from atmospheric temperature up to the temperature at which the partial pressure of the vaporized aqueous formaldehyde under the operation conditions of the column is no more than about 50 percent of the total gas pressure of the gas leaving the top of the column or in other words the temperature at which the gas leaving the top of the column contains no more than about 50 mol percent of vapors of the aqueous formaldehyde. Preferably the temperature is selected so that, under the operating conditions of the column, the gas leaving the top of the column comprises about 20 to about 40 mol percent of vapors of aqueous formaldehyde. Advantageously the column is operated under conditions such that the temperature of the column is in the range of about 60 to about 85° C. and more preferably in the range of about 65 to about 80° C. Similarly the weight ratio of stripping gas to aqueous formaldehyde solution passed through the column per unit time is selected so that under the operating conditions of the column the gas mixture leaving the column contains no more than about 50 mol percent of vapors of aqueous formaldehyde and preferably contains from about 20 to about 40 mol percent. In practice, the inert gas stream in the stripping column is advantageously maintained at a pressure above atmospheric pressure, preferably in the range of about 1.01 to about 2 atmospheres and the ratio of gas entering the stripping column to aqueous formaldehyde solution added to the stripping column from the first stage absorption stage is advantageously in the range of about 0.5 to about 2.5 by weight per unit time and is preferably in the range of about 1.0 to about 2.0.

In general the absorber can contain any number of absorption or scrubber stages for absorption of the reaction products of the oxidative dehydrogenation of methanol. Conveniently from 2 to 4 absorption stages each equipped with a recirculation loop and cooling system may be used. Sufficient water is continuously added to the system to maintain the desired formalin product concentration, and the temperatures and concentrations of the aqueous formaldehyde solutions in the stages are preferably maintained at levels for efficient absorption of formaldehyde and methanol from the reaction gas stream without formation of paraform in the stages. Part of the circulating stream of at least the first absorption stage is passed to the stripping column. Preferably none of the aqueous formaldehyde solution passed to the stripping column from the first absorption stage is returned to the absorber. It is preferably taken off at the bottom of the stripping column as formalin product. Preferably part of the recirculating stream of at least the first two absorption stages is passed to the stripping column, the points of entry being intermediate to top and bottom of the stripping column with the more dilute aqueous formaldehyde solution entering near the top of the column and the more concentrated solution entering near the bottom while at the same time the more dilute aqueous formaldehyde solution after descent in the stripping column is partly drawn off as a side stream above the entry point for the more concentrated solution and added to the circulation loop of the prior more concentrated aqueous formaldehyde absorption stage to maintain the concentration of formaldehyde in that absorption stage at a level to avoid formation of paraform at the particular temperature of the stage. Where part of the aqueous formaldehyde solution in an absorption stage other than the first absorption stage is supplied to the stripping column, the side stream from the stripping column may provide the only route whereby formaldehyde solution from that absorption stage can flow to the prior absorption stage containing more concentrated aqueous formaldehyde. While the stripper column preferably has at least two formaldehyde streams entering it from the absorber it can have as many entering streams as there are absorption stages in the absorber, the streams providing a formaldehyde concentration gradient in the stripping column.

In order to obtain significant removal of methanol from the aqueous formaldehyde by means of the stripping column without excessive removal of formaldehyde, the stripping column should comprise at least about 1.5 theoretical transfer units and preferably about 3 or more theoretical transfer units. The number of theoretical transfer units is determined from the following relationship:

$$NTU = (P_t - P_b)/[\tfrac{1}{2}(\Delta P_t + \Delta P_b)]$$

where $NTU$ = number of transfer units in the stripping column under steady state conditions, $P_t$ = vapor pressure of methanol in the gas stream emerging from the top of the stripping column, $P_b$ = vapor pressure of methanol in the gas stream entering the bottom of the stripping column, $\Delta P_t = P_t(e) - P_t$ $P_t(e)$ = equilibrium vapor pressure of methanol for the aqueous formaldehyde/methanol solution at the top of the column, at the temperature at the top of the column, $\Delta P_b = P_b(e) - P_b$ $P_b(e)$ = equilibrium vapor pressure of methanol for the aqueous formaldehyde/methanol solution at the bottom of the column, at the temperature at the bottom of the column.

The equilibrium vapor pressures are determined from standard vapor liquid equilibrium data, for example they may be obtained from data stored in the data base sold by Monsanto under the registered trademark Flowtran.

In aqueous formaldehyde solutions a methanol-methyl hemiformal-polyoxymethylene glycol monomethyl ether equilibrium exists and favors the hemiformals. The equilibrium can be displaced towards methanol by raising the temperature and by dilution of the formaldehyde solution with water. Methanol can be readily removed from dilute aqueous formaldehyde solutions by fractional distillation. However with concentrated solutions of aqueous formaldehyde which are gaining commercial favor, wherein the formaldehyde concentration is above about 40 weight percent and particularly wherein the formaldehyde concentration is above about 50 weight percent, processes to remove methanol and in particular the stripping process of the present invention to remove methanol at the relatively low temperatures used with the purpose of conserving energy, is more difficult because most of the methanol is chemically combined as hemiformals at these temperatures and, although reversal of the methanol hemiformal reaction occurs progressively with the removal of methanol from the solutions, the rate of reversal is rather low. Efficient removal of methanol in a stripping column comprising conventional packaging or tray columns would require an excessively high column. It is therefore advantageous to increase the residence time of the aqueous formaldehyde in the stripping column by any convenient means to allow equilibrium reversal of the methanol hemiformal reaction to occur. Preferably residence zones are introduced to allow the aqueous formaldehyde solution to remain quiescent out of contact with the stripping gas generally for at least about 4 minutes until a significant concentration of free methanol has been established. The column then becomes a series of stripping zones separated by residence zones, with the free methanol being generated by reversal of the methanol hemiformal reaction in the residence zones. One way to obtain quiescent residence zones is by introduction into the column of a number of chimney trays which are essentially overflow liquid trays with gas chimneys to allow the stripping gas ascending to pass by the aqueous formaldehyde solution held in the chimney trays. Another way is by means of circulation loops placed at intervals along the stripping column, the loops being equipped with reservoirs of suitable size to isolate the formaldehyde solution from the gas stream for the desired time. Thus with stripping columns comprising conventional packing or trays such as sieve trays, glass trays, bubblecap trays or valve trays to provide intimate contact between the aqueous formaldehyde solution and the stripping gas for efficient entrainment of methanol by the gas stream, it is advantageous to include residence zones at intervals in the column to reduce the height of the column required for efficient stripping of methanol. For example a 30 meter stripping column capable of handling about 5 metric tons of formalin product per hour, provides about four theoretical transfer units determined by means of the relationship set forth above, for the stripping of methanol when it is packed with 21 meters of Pall ring packing divided into 5 zones with each zone separated with a chimney tray of 10 cm. depth, providing a residence time of about 6 minutes in each residence tray. Similarly a 30 meter stripping column containing 45 sieve trays can provide about four theoretical transfer units when 4 residence trays each providing a residence time of about 6 minutes are placed at intervals along the column. Thus by means of the residence zones, transfer units of height in the range of about 1 to about 10 meters are readily obtained and allow the desired weight ratio of gas to liquid passing through the stripping column per unit time to be achieved.

The inert stripping gas which emerges from the stripping column entraining methanol, formaldehyde and water also entrains small amounts of hydrogen and carbon dioxide carried over from the absorption train. The gas is advantageously treated to remove the condensible components for example by scrubbing the gas with a cooled recirculated solution of aqueous formaldehyde to which water is constantly added and from which a portion is constantly taken off and passed to the circulation loop of the last absorption stage of the absorber. The amount of water added is adjusted to maintain the desired concentration of water throughout the entire system and to provide for the desired concentration of aqueous formaldehyde product. The treated gas can then be passed through a condenser to form an aqueous formaldehyde-methanol solution which is relatively rich in methanol and can be advantageously volatilized and recirculated to the methanol reactor. Because a major portion of the methanol present in the aqueous formaldehyde solution in the stripper column can be advantageously removed by the stripping action, the aqueous formaldehyde-methanol solution recycled to the reactor is characterized by a methanol to formaldehyde mol ratio of at least about 0.25 and a ratio of at least about 0.45 can be readily achieved. The mol ratio is generally at least about 10 times higher than the ratio of the starting solution. A minor fraction of the inert gas stream emerging from the condenser can advantageously be bled from the system, to avoid build up of the hydrogen gas and the bleed can be combined with the off-gas which emerges from the absorber and can be incinerated. The remainder of the inert gas stream is passed to the bottom of the stripping column for recirculation.

Optionally the inert gas which emerges from the stripping column can be passed to a partial condenser and the condensate can be returned to the top of the stripping column. In this manner, most of the formaldehyde and water is condensed and returned as a reflux to the stripping column while the inert gas stream retains most of the methanol removed from the aqueous formaldehyde solution in the stripping column. When the aqueous formaldehyde condensate is refluxed to the stripping column in this manner, the stripping column can advantageously be equipped with a top stage comprising a contact zone for intimate contact between the ascending inert gas stream and the descending aqueous formaldehyde reflux and a residence zone above the entry port for the most dilute aqueous formaldehyde solution entering the stripping column from the absorption train. The inert gas stream emerging from the partial condenser is then passed through a condenser and the condensate comprising mostly methanol can be volatilized and added to the reaction gas stream. The methanol condensate can advantageously have a methanol to formaldehyde mol ratio of at least about 0.6 and a ratio of at least about 1.0 can be readily achieved, and the mol ratio of recirculated formaldehyde to total methanol in the reaction gas stream can advantageously be less than about 0.035 and indeed less than about 0.03 to avoid unnecessary recycling of formaldehyde.

In comparison with a fractional distillation column for removal of methanol from the aqueous formaldehyde solution produced in the absorber, the gas-stripping process of the present invention can reduce the energy requirement for methanol removal by about 50 percent or more without sacrifice in separating efficiency. Advantageously for a balance in energy savings and separating efficiency, the stripping column is maintained at a temperature in the range of about 60° to about 85° C., and more preferably in the range of about 65° to about 80° C. and the ratio of stripping gas fed into the bottom of the stripping column to the most concentrated aqueous formaldehyde solution fed to the lower part of the stripping column from the absorber is in the range of about 0.5 to about 2.5 by weight per unit of time and more preferably in the range of about 1.0 to about 2.0.

Since the stripping column is operated at a relatively low temperature and since the reflux returned to the stripping column is a very minor fraction of the total amount of aqueous formaldehyde solution in the stripping column, the heat required to maintain the stripping column at the operating temperature can be readily supplied by the absorption solution from the first stage of the absorber and no external source of heat may be required.

The process may be carried out by the following method A (FIG. I): Air, methanol vapor and water vapor are charged continuously through an inlet 1 and fed via line 3 into a reactor 4 equipped with a silver catalyst bed. After reaction in 4, the reaction mixture passes via connecting line 5 into the first column 6 of a two stage absorber. A part of the formaldehyde solution formed in 6 is passed via lines 7 and 8 to a stripping column 9 comprising stages 9a, 9b, 9c, 9d and 9e, line 8 entering column 9 at the top of stage 9c. Concentrated aqueous formaldehyde of low methanol content is discharged continuously from the stripping column through line 10. The off-gas from the first absorption stage 6 passes via connecting line 11 into the second absorption stage 12 where it meets a dilute solution of aqueous formaldehyde and issues at the top of the absorber. A part of the formaldehyde solution formed in 12 is passed via lines 13 and 14 to the stripping column 9 entering the column at the top of stage 9e and flowing down the column countercurrent to the stripping gas stream. Part of the formaldehyde solution descending in the stripping column is drawn off at the bottom of stage 9d and flows via connecting line 15 to section 21 of the circulation loop 16, 17, 20, 21 of absorption stage 6. Part of product stream 10 is circulated via lines 18 and 19 through heat exchanger 17 and is returned to the top of stage 9a of the stripping column to provide a heat source for the stripping gas entering the stripping column through line 25 and passing up through stage 9a. The stripping gas emerges from the top of the stripping column and passes through line 26 and countercurrently in scrubber 27 to a circulated dilute aqueous formaldehyde solution with water make-up added through line 28. The aqueous solution formed in scrubber 27 passes through line 29 to section 33 of the circulating loop 30, 31, 32 and 33 of the second absorption stage. The stripping gas stream passes from the scrubber through line 35 to condenser 37 and moves countercurrently to a water stream added through line 36. The aqueous condensate of methanol, and formaldehyde passes through line 38 to vaporizer 39 and is added to the reaction gas stream 3 via line 2. The gas stream emerging from the condenser passes via lines 40 and 42 through blower 23 and heat exchanger 24 and enters the bottom of the stripping column 9 through line 25. A partial bleed of the circulating gas through line 41 to limit the build-up of hydrogen is compensated with addition of fresh inert gas through line 22.

Alternatively the process may be carried out by method B (FIG. 2): air and water vapor through line 101 and methanol vapor through line 140 are charged continuously via line 102 to a reactor 103. After reaction in 103, the reaction mixture passes via connecting line 104 into the first stage 105, of the absorber, then via line 109 to columns 110 and 114 and emerges through line 115 as an off gas comprising a major proportion of nitrogen and minor proportions of hydrogen and carbon dioxide. The off-gas is passed to an incinerator. The absorption stages 105, 110 and 114 are equipped with circulating loops 106, 107 and 108, 111, 112 and 113 and 116, 117 and 118 respectively. Sufficient water is added through line 119 to section 118 of the circulating loop of absorption stage 114 to maintain a water balance in the system and to provide formalin product of the desired concentration. The aqueous formaldehyde solutions in the absorption stages are circulated to provide flow countercurrent to the reaction product gas stream. The temperatures and concentrations of the aqueous formaldehyde solutions in the three absorption stages are maintained at levels to enhance the absorption of formaldehyde from the reaction gas stream and to avoid the formation of paraform. Portions of the aqueous formaldehyde stream 106 and 111 are passed via lines 120 and 125 respectively to stripping column 121 consisting of stages 121a, 121b, 121c, 121d and 121e. Line 120 enters column 121 at the top of stage 121b and line 125 at the top of stage 121d. Part of the solution which descends through stage 121c is taken off as a side stream and passed via line 126 to section 108 of the circulating loop of absorption stage 105. Part of the product solution which emerges from the bottom of the stripping column in line 122 is circulated via line 123 to heat exchanger 107 in the circulation loop of absorption stage 105 and is returned via line 124 to the top of stage 121a of the stripping column to provide a heat source for the stripping gas which enters the column through line 127 at the foot of stage 121a and ascends countercurrently to the formaldehyde solution in the column. The stripping gas emerges from column 121 via line 128 and is passed to a partial condenser 130 which condenses much of the formaldehyde and water in the gas stream and returns them via line 129 to the top of stripping column 121. The gas stream proceeds from the partial condenser via lines 131 and 133 through a condensing system consisting of a precondenser 132 and a condenser 134 and emerges virtually free of formaldehyde, methanol and water as stream 141. Partial bleed of stream 141 through 142 to prevent build-up of hydrogen gas in the stripping gas is compensated with a make-up of fresh inert stripping gas added through line 143. The stripping gas is then recirculated through line 127. The condensate obtained from the precondenser and condenser, comprising mostly water and methanol is collected in distillate receiver 137 via lines 135 and 136, and is passed with the main methanol charge added via line 144, through line 138 to vaporizer 139 and then via lines 140 and 102 to the reactor. Water is added via line 145.

In the embodiments of the invention, the absorber comprises at least two stages or columns. In the first stage or column, the aqueous formaldehyde solution which circulates in the circulation loop preferably contains from about 45 to about 70 weight percent of formaldehyde, from about 1.0 to about 6 weight percent methanol and from about 25 to about 49 weight percent of water; in the circulation loop of the second stage, the aqueous formaldehyde preferably contains from about 25 to about 40 weight percent formaldehyde, from about 2.5 to about 7.5 weight percent of methanol and from about 52.5 to about 67.5 weight percent water; and in the circulation loop of a third stage, the aqueous formaldehyde preferably contains from about 10 to about 20 weight percent formaldehyde, from about 4 to about 15 weight percent methanol and from about 65 to about 84 weight percent water. The absorption is preferably carried out at temperatures in the range of about 60° to about 90° C. in the first absorption stage, about 20° to about 60° C. in the second stage and about 10° to about 25° C. in the third stage. Advantageously the aqueous formaldehyde solution supplied to the stripping column from the second absorption stage and optionally from succeeding absorption stages may be heated prior to entry into the stripping column to a temperature within the range of from about 10° C. below, up to about the temperature of the formaldehyde solution at the bottom of the stripping column.

The formaldehyde solution manufactured by the process of the invention, is a disinfectant, tanning agent, reducing agent and a starting material for the manufacture of organic chemicals and synthetic resins and adhesives.

The invention is further illustrated but is not intended to be limited by the following examples in which parts and percentages are by weight unless specified otherwise.

EXAMPLE 1

A plant comprising a reactor, absorber, stripping column, scrubber and condenser as described for method A is employed. The stripper column is 27.7 meters high and comprises 21 meters of Pall ring packing in 5 zones, the zones being separated by chimney trays of 10 cm. depth. Per hour a gaseous mixture of 7000 parts of methanol, 2795 parts of water, 708 parts of formaldehyde and 11058 parts of air is fed continuously to the reactor. Per hour an aqueous formaldehyde solution containing 5284 parts of formaldehyde, 171 parts of methanol, 3401 parts of water, 36 parts of nitrogen, 0.3 parts of hydrogen and 7 parts of carbon dioxide at a temperature of 86° C. is introduced continuously into the stripper column from the circulating loop of the first absorption stage of the absorber and passed downward in the stripping column, and an aqueous formaldehyde solution containing 3179 parts of formaldehyde, 390 parts of methanol, 5108 parts of water, 68 parts of nitrogen, 0.5 parts of hydrogen and 26 parts of carbon dioxide at a temperature of 65° C. is introduced continuously into the stripper column from the circulating loop of the second absorption stage and passed downward in the stripper column. Per hour, an aqueous formaldehyde solution containing 1719 parts of formaldehyde, 87 parts of methanol, 2547 parts of water, 27 parts of nitrogen, 0.1 parts of hydrogen and 6 parts of carbon dioxide is drawn off from the side of the stripping column above the entry port for the first absorption solution and is passed to the first absorption stage. Per hour 11176 parts of stripping gas comprising 10067 parts of nitrogen, 9 parts of formaldehyde, 32 parts of methanol, 104 parts of water, 92 parts of hydrogen and 872 parts of carbon dioxide is introduced into the bottom of the stripping column and passed upward. The temperature of the stripping column is 74° C. at the bottom and 71° C. at the top. The gas stream emerging from the stripper column comprises 1063 parts of formaldehyde, 404 parts of methanol, 2606 parts of water, 10080 parts of nitrogen, 93 parts of hydrogen and 885 parts of carbon dioxide. The gas stream is passed to a scrubber to which 250 parts of water is added continuously per hour. The aqueous formaldehyde solution formed in the scrubber, containing 347 parts of formaldehyde, 34 parts of methanol and 645 parts of water is passed to the second absorption stage. The gas stream emerging from the scrubber is then passed through a condenser countercurrent to a downward flow of circulating aqueous formaldehyde made up with 30 parts of water per hour and aqueous formaldehyde solution is drawn off at a rate of 3221 parts per hour comprising 708 parts of formaldehyde, 337 parts of methanol, 2137 parts of water, 27 parts of nitrogen and 12 parts of carbon dioxide and is recycled to the reaction gas stream. 9332 parts of aqueous formaldehyde solution containing 5690 parts of formaldehyde, 103 parts of methanol and 3462 parts of water is drawn off from the bottom of the stripping column as product. The yield is 88% and the conversion is 98.5%. The methanol content is 1.1 percent. The energy requirement for the stripping column is 1.0 gigajoule per metric ton of product. The net energy balance for the process is −89 kilojoules per metric ton of product. The mol ratio of recycled methanol to recycled formaldehyde is 0.45.

EXAMPLE 2

Figure 2:
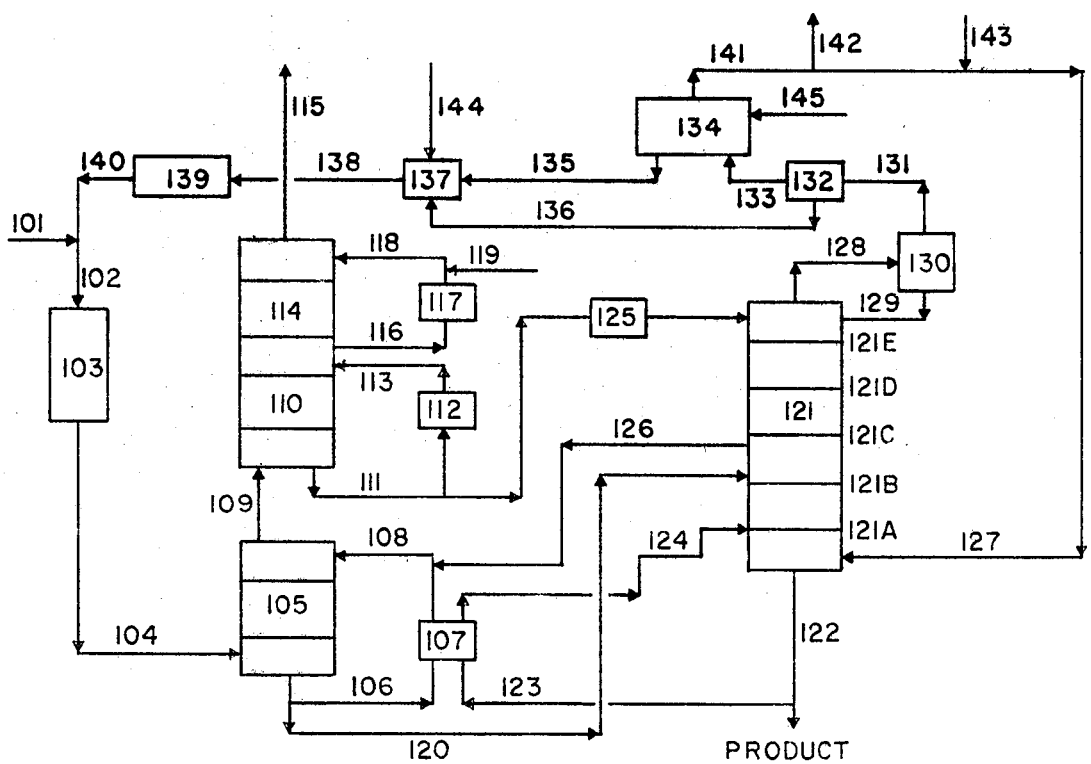

A plant comprising a reactor, absorber, stripping column, partial condenser and condenser system as set forth in FIG. 2 is used. The stripper column is 27.7 meters high and comprises 21 meters of Pall ring packing in 5 zones, the zones being separated by chimney trays of 10 cm. depth. Per hour, a gaseous mixture of 7001 parts of methanol, 2795 parts of water, 223 parts of formaldehyde, and 11051 parts of air is fed continuously to the reactor. Per hour an aqueous formaldehyde solution containing 4532 parts of formaldehyde, 163 parts of methanol, 3358 parts of water, 35 parts of nitrogen, 0.3 parts of hydrogen and 7 parts of carbon dioxide at a temperature of 88° C. is introduced continuously into the stripper column from the circulating loop of the first absorption stage of the absorber and passed downward in the stripping column, and an aqueous formaldehyde solution containing 2325 parts of formaldehyde, 321 parts of methanol, 4032 parts of water, 46 parts of nitrogen, 0.4 parts of hydrogen and 14 parts of carbon dioxide at a temperature of 65° C. is introduced continuously into the stripper column from the circulation loop of the second absorption stage and passed downward in the stripping column. Per hour, an aqueous formaldehyde solution containing 1210 parts of formaldehyde, 66 parts of methanol, 2043 parts of water, 23 parts of nitrogen, 0.1 parts of hydrogen and 4 parts of carbon dioxide is drawn off from the side of the stripping column above the entry port for the first absorption solution and is passed to the first absorption stage. Per hour 11551 parts of stripping gas comprising 10521 parts of nitrogen, 0.4 parts of formaldehyde, 24 parts of methanol, 142 parts of water, 96 parts of hydrogen and 768 parts of carbon dioxide is introduced into the bottom of the stripping column and passed upward. The temperature of the stripping column is 77° C. at the bottom and 72° C. at the top. The gas stream emerging from the stripper column comprises 986 parts of formaldehyde, 529 parts of methanol, 2764 parts of water, 10519 parts of nitrogen, 96 parts of hydrogen and 775 parts of carbon dioxide. The gas stream is passed to a partial condenser and the partial condensate comprising 765 parts of formaldehyde, 199 parts of methanol and 1885 parts of water is returned to the top section of the stripping column. The gas stream emerging from the partial condenser is then passed through a precondenser and countercurrent in a final condenser to a circulated aqueous stream made up with 1000 parts of water per hour. The aqueous formaldehyde solution containing 223 parts of formaldehyde, 306 parts of methanol, and 1745 parts of water is collected in a distillate receiver and mixed with 6692 parts of fresh methanol for recycle to the reaction gas stream. 10245 parts of aqueous formaldehyde solution containing 5426 parts of formaldehyde, 112 parts of methanol and 4609 parts of water is drawn off from the bottom of the stripping column as product. The yield is 87% and the conversion is 98.4%. The methanol content is 1.1 percent. The energy requirement for the stripping column is 0.87 gigajoule per metric ton of product. The net energy balance for the process is −0.1 megajoule per metric ton of product. The mol ratio of recycled formaldehyde to total methanol fed to the reactor is 0.032 and the mol ratio of recycled methanol to recycled formaldehyde is 1.39.

EXAMPLE 3

Example 2 is repeated with a stripping column temperature of 85° C. at the bottom and 79° C. at the top. A 53.5 weight percent formalin solution containing 0.79 percent methanol is obtained as the product. The yield is 88 and the conversion is 99%. The energy requirement for the stripping column is 1.522 gigajoules per metric ton of product. The net energy balance for the process is +1204 megajoules per metric ton of product.

EXAMPLE 4

Example 2 is repeated with a stripping column temperature of 65° C. at the bottom and 59° C. at the top. A 52.9 weight percent formalin solution, containing 1.63 percent methanol is obtained as the product. The yield is 86% and the conversion is 98%. The energy requirement for the stripping column is 0.451 gigajoules per metric ton of product. The net energy balance for the process is −0.1 megajoules per metric ton of product.

What is claimed is:

1. A process for the manufacture of an aqueous solution of formaldehyde comprising the steps of:
(a) oxidatively dehydrogenating methanol with air in the presence of a silver or copper catalyst and steam at elevated temperature;
(b) absorbing the reaction product in an absorption train comprising one or more absorption stages in series to form an aqueous formaldehyde solution containing free and combined methanol; and
(c) stripping the methanol from the aqueous formaldehyde solution with a counter-current inert gas stream in a stripping column comprising at least about 1.5 theoretical transfer units for methanol stripping, the stripping being carried out at a temperature and at a ratio of stripping gas to aqueous formaldehyde to provide a concentration of vapors of aqueous methanolic formaldehyde in the gas emerging from the stripping column of no more than about 50 mol percent.

2. The process of claim 1 wherein the stripping column comprises at least about three theoretical transfer units.

3. The process of claim 1 or 2 wherein the height of the theoretical transfer unit is in the range of about 1 to about 10 meters.

4. The process of claim 3 wherein the temperature of the stripping column is in the range of about 60° to about 85° C.

5. The process of claim 3 wherein the stripping column contains residence zones providing average residence times of at least about 4 minutes per zone.

6. The process of claim 5 wherein the residence zones are chimney trays.

7. The process of claim 5 wherein the reference zones are circulation side loops and reservoirs.

8. The process of claim 3 wherein the inert gas is selected from the group consisting of nitrogen, helium, neon and argon.

9. The process of claim 3 wherein the weight ratio of inert gas to aqueous formaldehyde from the first absorption stage entering the stripping column per unit time is in the range of about 0.5 to about 2.5.

10. The process of claim 3 wherein the weight ratio of inert gas to aqueous formaldehyde from the first absorption stage entering the stripping column per unit time is in the range of about 1.0 to about 2.0.

11. The process of claim 3 wherein the absorption train comprises two or more absorption stages, wherein portions of the circulating aqueous formaldehyde stream drawn from the bottom of at least the first two absorption stages are passed as separate streams to the stripping column with the more dilute streams entering near the top and the more concentrated streams entering near the bottom of the stripping column to provide a concentration gradient within the stripping column and wherein a portion of each of the more dilute streams descending the stripping column is drawn off as a side stream before it reaches the next more concentrated formaldehyde solution entering the stripping column and is added to the circulation loop of the next more concentrated circulating stream prior to re-entry of the next more concentrated circulating stream into the absorption column.

12. The process of claim 11 wherein the number of absorption stages is in the range of 2 to 4 and wherein aqueous formaldehyde solution is supplied from at least the first two absorption stages to the stripping column.

13. The process of claim 11 wherein the stripping gas which emerges from the stripping column is treated with an aqueous formaldehyde solution to absorb formaldehyde and water from the gas and the aqueous formaldehyde solution is then passed to the circulation loop of the final absorption stage in the absorption train prior to its reentry into the absorption column.

14. The process of claim 13 wherein the stripping gas after treatment with aqueous formaldehyde is passed through a condenser and the condensed aqueous methanol formaldehyde solution which forms is recycled to the oxidative-dehydrogenation reactor.

15. The process of claim 14 wherein the mol ratio of recycled methanol to recycled formaldehyde is at least 0.25.

16. The process of claim 11 wherein the stripping gas which emerges from the stripping column is passed through a partial condenser and the condensed aqueous formaldehyde solution which forms is refluxed to the stripping column.

17. The process of claim 16 wherein the stripping gas which emerges from the partial condenser is passed through a condenser and the condensed aqueous methanol formaldehyde solution which forms is recycled to the oxidative-dehydrogenation reactor.

18. The process of claim 17 wherein the mol ratio of recycled methanol to recycled formaldehyde is at least about 0.6.

19. The process of claim 17 wherein the mol ratio of recycled formaldehyde to total methanol fed to the reactor is less than 0.035.

* * * * *